(12) United States Patent
Story et al.

(10) Patent No.: US 8,709,142 B2
(45) Date of Patent: Apr. 29, 2014

(54) INK FORMULATION AND MANUFACTURE THEREOF

(75) Inventors: Mytia V. Story, Englewood, NJ (US); Darlene P. Story, Englewood, NJ (US)

(73) Assignee: EndoChoice, Inc., Alpharetta, GA (US)

(*) Notice: Subject to any disclaimer, the term of this patent is extended or adjusted under 35 U.S.C. 154(b) by 276 days.

(21) Appl. No.: 13/356,395

(22) Filed: Jan. 23, 2012

(65) Prior Publication Data
US 2013/0098265 A1    Apr. 25, 2013

Related U.S. Application Data

(60) Provisional application No. 61/549,393, filed on Oct. 20, 2011.

(51) Int. Cl.
*C09D 11/00*    (2006.01)

(52) U.S. Cl.
USPC ............................................. 106/31.03

(58) Field of Classification Search
CPC ...................................... C09C 11/00
USPC ......................................... 106/31.03
See application file for complete search history.

(56) References Cited

U.S. PATENT DOCUMENTS

| | | | |
|---|---|---|---|
| 3,258,355 A | 6/1966 | Andries | |
| 5,522,922 A | 6/1996 | Furusawa | |
| 5,928,419 A | 7/1999 | Uemura | |
| 6,013,122 A * | 1/2000 | Klitzman et al. | 106/31.03 |
| 6,280,702 B1 | 8/2001 | Carter | |
| 6,599,496 B2 | 7/2003 | Carter | |
| 6,800,122 B2 * | 10/2004 | Anderson et al. | 106/31.03 |
| 7,435,524 B2 * | 10/2008 | Anderson et al. | 106/31.03 |
| 7,510,603 B2 * | 3/2009 | Michel | 106/31.03 |
| 8,420,044 B2 * | 4/2013 | Bergemann et al. | 423/449.2 |
| 2002/0031474 A1 | 3/2002 | Carter | |
| 2011/0177202 A1 | 7/2011 | Christiansen | |

FOREIGN PATENT DOCUMENTS

WO    2013058810 A1    4/2013

OTHER PUBLICATIONS

International Search Report for PCT/US12/22235, May 4, 2012.

* cited by examiner

*Primary Examiner* — Helene Klemanski
(74) *Attorney, Agent, or Firm* — Novel IP (57) ABSTRACT

An ink formulation for marking living tissue comprises a dispersion of carbon black pigment particles encapsulated in water soluble shells, mixed with a pharmaceutically accepted carrier, such as water, and a preservative. A dispersion formulation is preferential to a suspension formulation for marking living tissue because the carbon particles of the dispersion formulation are less likely to aggregate and sediment over time. In addition, the absence of large quantities of additives makes a dispersion formulation less reactive to living tissue, further enhancing its appeal as a biological marker.

20 Claims, 3 Drawing Sheets

INK FORMULATION AND MANUFACTURE THEREOF

CROSS REFERENCE

The present application relies on U.S. Provisional Application No. 61/549,393 filed on Oct. 20, 2011 and is hereby incorporated by reference.

FIELD

The present application is directed toward an ink formulation. More particularly, the present application is directed toward an ink formulation that is in the form of a dispersion and can be used for marking living tissue, along with a method for preparing the ink dispersion formulation.

BACKGROUND

Ink formulations comprise mixtures of insoluble particles in a liquid vehicle and are widely used as a method of administering solid particles. Permanent and semi-permanent inks are suspensions of insoluble colorants. Additionally, many liquid oral medications are suspensions of insoluble active ingredients. A common concern in such a system is that insoluble particles tend to separate out of the mixture over time. Stability can affect the appropriate administration of a product.

In a mixture, insoluble solids inside a liquid matrix tend to aggregate and particle sedimentation can occur. Aggregation, the process by which smaller particles in a mixture combine together or flocculate, becomes more likely with increased particle size and concentration. Sedimentation, the process by which the particles gather at the bottom of the mixture due to density, becomes more likely as particles aggregate.

Suspensions and sol type dispersions are two common forms of mixtures of insoluble particles in a liquid vehicle. Mud, which is soil suspended in water, is a common suspension and blood is a common sol type dispersion.

Suspensions utilize suspending and rheology modifiers to suspend solids in a liquid matrix. The liquid matrix can be made thicker and suspending agents can be added as needed. This allows particles to be trapped in the web of the matrix for a time, lowering the rate of sedimentation. This is the method used when making a suspension such as many liquid oral medications.

Dispersions utilize particles that have been ground smaller and coated with a dispersing aid prior to addition to the liquid matrix. The coating is such that it has an affinity toward the liquid matrix which helps prevent the particles from aggregating. The insoluble particles can then be dispersed in the matrix and the coating on the particles allows for the particles to have a greater affinity for the matrix.

Dispersions are considered better for many pharmaceutical preparations because dispersions do not adhere to the normal laws of suspensions, such as Stoke's law. This allows for stability with fewer or no vehicle thickening agents. When flocculation is disregarded, sedimentation velocity can be seen in terms of Stoke's law:

$$v = d2(\rho_s - \rho_1)g/18\eta$$

Where, v=Terminal settling velocity
d=Diameter of the settling particle
$\rho_s$=Density of the settling solid (dispersed phase)
$\rho_1$=Density of the liquid (dispersion medium)
g=Gravitational acceleration
$\eta$=Viscosity of the dispersion medium By this law, the terminal settling velocity increases as the viscosity of the medium decreases. When the vehicle is water, thickeners are needed to create a more stable suspension. As more additives are introduced to the mixture, its viscosity increases resulting in greater stability. However, the higher viscosity lowers the ease of application and pourability of the mixture and re-dispersibility of the sediment. Since it is also known that any additive increases the chance of allergic reaction and can affect any active ingredient in the formulation, additives can limit the effectiveness and affect the dosage of certain formulations, particularly pharmaceutical preparations. Further side by side trials comparing dispersion stability to the stability of a like suspension is of great benefit to improving on pharmaceutical formulations.

Dispersions have a number of qualities that make them better candidates than suspensions for use in ink formulations. For example, there is very little to prevent aggregation and sedimentation in a suspension. Insoluble particles present in typical suspensions are large enough for sedimentation. Smaller insoluble particle size improves biocompatibility and reduces the speed of sedimentation. With dispersions, milling is used to create smaller particles than those used in suspensions. In addition, dispersions contain particles that have been encapsulated within a coating that has a higher affinity for the surrounding liquid than for other particles. The milling process in the dispersion allows for smaller particles while the encapsulation of particles helps slow the rate of aggregation and allows those particles to have a greater affinity for the liquid matrix. If properly made, a dispersion prevents aggregation and sedimentation, resulting in a more stable mixture with a more consistent density.

During certain medical procedures, there is a need to mark living human tissue with a substantially permanent ink. For example, during an endoscopy procedure, if lesions are found in a gastrointestinal (GI) tract of a patient, it is advantageous to mark the lesions to enable enhanced localization during surgery or subsequent endoscopies. Usually, a staining agent or ink is injected into a luminal mucosal surface for marking specific regions of the GI tract.

India ink has been commonly used as a staining agent for marking living tissue over several decades. It is composed of a colloidal suspension of carbon particles in a solution of organic and nonorganic substances used as stabilizing diluants and surfactants. Other dyes for marking tissue include carbon particle suspension, methylene blue, indigo carmine, toluidine blue, lymphazurin, hematoxylin, eosin, and indocyanine green (ICG). It has been observed that India ink is a preferred staining agent in terms of safety, efficacy, and ease of use. Moreover, India ink is a more preferable staining agent due to its substantial permanence when compared to other approved dyes. However, the use of India ink as a living tissue staining agent is not without its drawbacks. For example, India ink stains containing higher concentrations of carbon have been known to cause inflammation and create abscesses in living tissue. Stains with lower concentrations of carbon often result in insufficient staining and therefore less than desirable tissue visualization.

Endoscopic dyeing agents other than India ink have been formulated to permanently stain living tissue without the associated side effects noted above. For example, U.S. Pat. No. 6,280,702, assigned to Chek-Med Systems, Inc., discloses an "endoscopic tissue staining composition comprising carbon pigment, suspending/viscosity-increasing agent in a pharmaceutically acceptable delivery vehicle, anti-foaming agent, and surfactant, said carbon pigment in an effective staining amount for internal mucosa and said suspending/viscosity-increasing agent in an effective amount for suspending carbon in solution and providing sufficient viscosity for endoscopic tissue staining" In addition, U.S. Pat. No. 6,599,496, also assigned to Chek-Med Systems, Inc., discloses an "endoscopic tissue staining composition comprising a carbon pigment and a suspending/viscosity-increasing agent in a pharmaceutically acceptable delivery vehicle, wherein said carbon pigment has a level of total polycyclic aromatic hydrocarbons of not greater than 0.5 ppm."

Conventional inks for marking living tissue, including India ink and formulations disclosed in the United States patents referenced above, are suspensions of carbon particles in a suspending agent. Typically, the process of forming suspensions involves increasing the viscosity of a suspending material, such as water, by using suspending/viscosity increasing agents and adding sufficient quantities of solubilizing agents to suspend carbon particles for a desired amount of time.

Suspensions are not an ideal choice for ink formulation for marking living tissue. This is because suspensions require a large number of additives in order to effectively suspend the carbon particles. The materials commonly used as additives in ink suspensions include large quantities of thickeners (5-25%), surfactants, and antifoaming agents. It is a common observation that in spite of using a variety of additives, the suspended carbon particles still have a tendency to precipitate within the suspension. Additionally, the use of large quantities of additives may cause the ink suspensions to become reactive to living tissue causing irritation and/or redness and swelling of the tissue. Typically, such reactions symptoms arise from allergic reactions which increase when the amount and variety of additives increase. Therefore, in patients with pre-existing problems, this can be extremely detrimental.

Hence, there is a need for an ink formulation for marking living tissue sites that is more stable than the available ink suspensions, while still providing a sufficient level of carbon to stain living tissue and not cause cell inflammation or cell death. There is also a need for an ink formulation that contains minimal or no additives such as thickeners, surfactants and antifoaming agents, thereby making the formulation non-reactive and safe for use with human tissue. Such an ink formulation can be put to a plurality of uses including, but not limited to, safe and effective marking of living tissue.

SUMMARY

In one embodiment, the present application discloses an ink formulation for marking living tissue, wherein said ink formulation is made by the following process: mixing a pharmaceutically accepted carrier with a preservative to form a carrier-preservative compound; pre-wetting a carbon pigment with a first emulsifying agent; mixing a second emulsifying agent with glycerin to form an emulsifier-glycerin compound; adding said emulsifier-glycerin compound to the pre-wet carbon and mixing until encapsulated carbon particles are formed; and mixing said carrier-preservative compound with said encapsulated carbon particles to form said ink formulation.

Optionally, the pharmaceutically accepted carrier is water. The water comprises between 85.00 and 92.00% of the total formulation by weight. The water comprises 91.73% of the total formulation by weight. The preservative is chosen from a group comprising 2-phenoxyethanol, benzyl alcohol, methyl/propyl paraben blend, and polyaminopropyl biguanide. The preservative comprises between 1.00 and 1.50% of the total formulation by weight. The preservative comprises 1.24% of the total formulation by weight. The carbon pigment is carbon black and the carbon black contains PAH in a range of 0.5 ppm or more. The carbon black comprises between 1.09 and 1.10% of the total formulation by weight. The carbon black comprises 1.09% of the total formulation by weight.

Optionally, the first and second emulsifying agents are chosen from a group comprising lecithin, soy lecithin, polyvinylpyrrolidone (PVP), emulsifying wax, and polysorbate 20. The first and second emulsifying agents comprise between 0.20 and 0.30% and between 1.00 and 2.50% respectively, of the total formulation by weight. The first and second emulsifying agents comprise 0.24% and 2.50% respectively, of the total formulation by weight. The glycerin comprises between 2.50 and 4.50% of the total formulation by weight. The glycerin comprises between 3.15% of the total formulation by weight.

In another embodiment, the present application discloses a method of preparing an ink formulation for marking living tissue, comprising the steps of: mixing a pharmaceutically accepted carrier with a preservative to form a carrier-preservative compound; pre-wetting a carbon pigment with a first emulsifying agent; mixing a second emulsifying agent with glycerin to form an emulsifier-glycerin compound; adding said emulsifier-glycerin compound into the pre-wet carbon and mixing until said carbon is dispersed; and mixing said carrier-preservative compound to said dispersed carbon.

Optionally, the mixing of the pharmaceutically accepted carrier with said preservative is performed at a high speed for approximately 2 minutes. The pre-wetting of the carbon pigment with the first emulsifying agent and the mixing of the second emulsifying agent with glycerin are performed separately and wherein both the pre-wetting of the carbon pigment with the first emulsifying agent and the mixing of the second emulsifying agent with glycerin are performed using a homogenizer. The adding of the emulsifier-glycerin compound into the pre-wet carbon and mixing until carbon is dispersed is performed using a rotor stator blender mixing machine for approximately 5 minutes at 2,000 to 3,000 rpm. The adding of the carrier-preservative compound to the encapsulated carbon compounds is performed using a rotor stator blender mixing machine for approximately 3 minutes at 2,000 to 3,000 rpm.

In another embodiment, the present application discloses an ink formulation for use on living tissue, having a total weight, comprising a pharmaceutically acceptable carrier, wherein said pharmaceutically acceptable carrier is in a range of 85% to 92% of the total weight; a preservative, wherein said preservative is in a range of 1.0% to 1.5% of the total weight; and carbon black, wherein said carbon black is in a range of 1.09% to 1.10% of the total weight, wherein particles of said carbon black are encapsulated by at least one of lecithin, soy lecithin, polyvinylpyrrolidone (PVP), emulsifying wax, polysorbate 20, or glycerin, and wherein said ink formulation is a dispersion of said preservative and carbon black in the carrier. Optionally, the carrier is water and the preservative is one of 2-phenoxyethanol, benzyl alcohol, methyl/propyl paraben blend, or polyaminopropyl biguanide. Optionally, the formulation does not include suspending agents, viscosity agents, surfactants, ceteareth 20, or antifoaming agents.

BRIEF DESCRIPTION OF THE DRAWINGS

These and other features and advantages of the present application will be further appreciated as they become better understood by reference to the detailed description when considered in connection with the accompanying drawing.

DETAILED DESCRIPTION

The present application is directed toward an ink formulation for marking living tissue. In one embodiment, the ink disclosed herein comprises a dispersion of carbon black pigment particles encapsulated in water soluble shells mixed with a pharmaceutically accepted carrier, such as water, and a preservative.

In order to remain dispersed within the carrier, the carbon black pigments are encapsulated with bi-polar molecules using, in at least one embodiment, emulsifiers. In various embodiments, the pigments are encapsulated by a variety of emulsifiers commonly known in the art. In one embodiment, the emulsifiers comprise lecithin and polyvinylpyrrolidone (PVP). In one embodiment, the lecithin is particularly soy lecithin and comprises no more than 0.20-0.30% by weight of the formulation while the PVP comprises no more than 1-2.5% by weight of the formulation. Both lecithin and PVP are widely used in the pharmaceutical industry and are considered very safe, even in large amounts. In another embodiment, an emulsifier is emulsifying wax. In another embodiment, an emulsifier is polysorbate 20.

In one embodiment, the preservative used in the dispersion is 2-phenoxyethanol. In other various embodiments, the preservative is chosen from a multitude of pharmaceutically accepted preservatives, including, but not limited to, benzyl alcohol, methyl/propyl paraben blend, and polyaminopropyl biguanide.

Since the ink formulation disclosed herein is a dispersion of carbon black pigment particles, the ink does not precipitate out, as it does in conventional tissue ink suspensions. The dispersion ink formulation and manufacturing process disclosed herein provide a stable marking agent and eliminate the need for suspending/viscosity agents, surfactant, ceteareth 20, and antifoaming agents, though, in some embodiments, one or more of these may be optionally added for ease of application; in other embodiments, the ink formulation expressly does not include suspending/viscosity agents, surfactant, ceteareth 20, or antifoaming agents. The dispersion of carbon black particles in the ink does not depend on the viscosity of a carrier solution, as is the case with suspension ink formulations commonly known in the art. Accordingly, the inventions disclosed herein enable the creation of staining agents with lower possible viscosities as the viscosity can be tailored to be most effective by application, rather than being tailored to optimize suspension.

It should be noted herein that viscosities for marking live tissues should be as low viscosity as possible to aid in application and accuracy of marking. For tattooing applications, however, viscosities vary more with the type of application. A thinner, less concentrated formulation can be used for lining versus using a thicker, higher concentration formulation can be used for filling in the lining. In any application, if more viscosity is required, any viscosity increasing agent may be employed. In formulations used for marking live tissues, such as the GI tract, glycerin is an appropriate viscosity modifier. In formulations used for tattoo applications, the viscosity is generally modified by changing the concentration of any of the ingredients in the formulation and modifying the way in which the ingredients are blended.

The present application is also directed toward a method of preparing the dispersion ink formulation used for marking living tissue described above. In one embodiment, the method of preparing the dispersion ink comprises the following steps. The preservative is added to the water phase. The carbon pigment is first pre-wet with lecithin. A mixture of PVP and glycerin is then added to the carbon pigment. This combination is then mixed slowly to the point at which the carbon particles become small enough so that the lecithin and PVP form micelles around the particles, effectively encapsulating the carbon in a water-soluble coating. At this point, the carbon capsules are already dispersed in the glycerin. This mixture is then slow mixed, so as not to break the carbon capsules, into the water. This preparation method requires fewer emulsifying agents, resulting in a lower chance of adverse reactions. In addition, the encapsulation aids in dispersing the carbon in the water without additives while also allowing for easier insertion into cells.

The present application is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the embodiments disclosed herein are to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
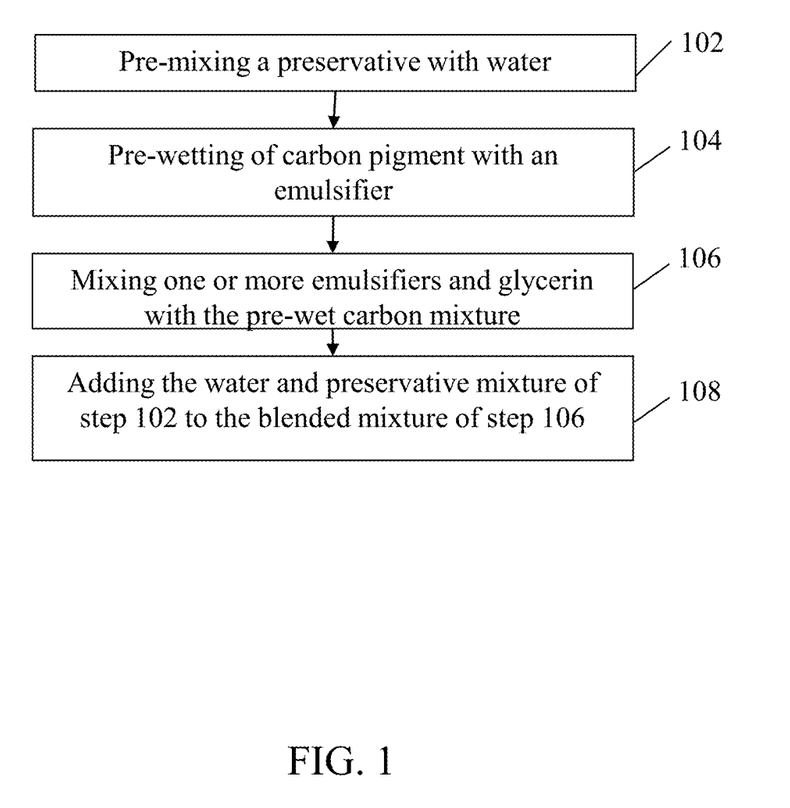
FIG. 1 is a flowchart illustrating exemplary steps of making an ink dispersion for marking living tissue, in accordance with one embodiment of the present application.

FIG. 1 is a flowchart illustrating the steps of a method of making an ink for marking living tissue, in accordance with an embodiment of the present invention. At step 102, a preservative is added to water to obtain a mixture. In various embodiments, water acts as a pharmaceutically acceptable carrier to carbon black pigments contained in the ink formulation of the present invention. In various embodiments, the preservative used is any pharmaceutically accepted preservative. Examples of the preservatives that may be used include, but are not limited to, 2-phenoxyethanol, benzyl alcohol, methyl/propyl paraben blend, and polyaminopropyl biguanide. In an embodiment, 2-phenoxyethanol is mixed with water in a mixer at a high speed for approximately two minutes or until the 2-phenoxyethanol is well blended with water. In one embodiment, a homogenizer is used and operated at a speed of 2,500 to 3,000 rpm for 2 to 5 minutes. In various embodiments, the quantities of water and 2-phenoxyethanol used in the ink formulation range between 85.00-92.00% and 1.00-1.50% respectively. In an embodiment, the quantities of water and 2-phenoxyethanol used in the ink formulation are 91.73% and 1.24% respectively.

At step 104, carbon black pigments are pre-wet with an emulsifier. One of ordinary skill in the art would appreciate that the carbon black pigments are sufficiently "pre-wet" when the carbon black pigments are moist without having visibly discernable clumps. In one embodiment, the carbon black pigment having polyaromatic hydrocarbons (PAH) in an amount equal to or greater than 0.5 ppm is used. In various embodiments, any emulsifier (material containing bipolar molecules) considered safe for use in the pharmaceutical industry may be used to encapsulate the carbon pigments. In various embodiments, materials such as soy lecithin, emulsifying wax, polyvinylpyrrolidone (PVP), or polysorbate 20 are used as emulsifiers. In an embodiment, the carbon black pigments are pre-wet with lecithin by mixing the carbon black pigments with lecithin at a slow speed using a homogenizer mixer. In one embodiment, the slow speed is in a range of 500 to 800 rpm. In various embodiments, the quantities of carbon black and lecithin used in the ink formulation range between 1.09-1.10% and 0.20-0.30% respectively. In an embodiment, the quantities of carbon black and lecithin used in the ink formulation are 1.09% and 0.24% respectively. The mixing is continued until the carbon pigments are wetted out.

At step 106, one or more emulsifiers are mixed with the pre-wet carbon mixture. In an embodiment, an emulsifier, such as PVP, is first mixed with a polyol (an alcohol containing multiple hydroxyl groups) glycerin, and then the subsequent mixture is added to the pre-wet carbon black pigments at step 106. The polyol may be glycerin, ethylene glycol, or sugar additives such as sorbitol. Glycerin is preferred because it is a simpler version of a polyol, stable, and generally unreactive. Glycerin is also sufficiently thin, allowing for a very small viscosity increase to the formulation. In various embodiments, the quantities of PVP and glycerin used in the ink formulation range between 1.00-2.50% and 2.50-4.50% respectively. In an embodiment, the quantities of PVP and glycerin used in the ink formulation are 2.50% and 3.15% respectively.

Upon mixing said materials containing bipolar molecules with the carbon black pigments, the lecithin and PVP form micelles around the carbon pigments, thereby encapsulating each carbon pigment in a water-soluble coating. In an embodiment, the emulsifiers and glycerin are mixed with the carbon black pigments using a mixing machine of a rotor stator blender variety, which is operated at approximately 2,000 to 3,000 rotations per minute for approximately five minutes or until the carbon black particles are completely dispersed in the glycerin.

At step 108 the water and preservative mixture obtained at step 102 (subsequently herein referred to as mixture A) is added to the blended mixture of carbon black, emulsifiers and glycerin obtained at step 106 (subsequently herein referred to as B). In various embodiments, mixture A and mixture B are mixed slowly so as not to break the carbon pigment capsules contained in mixture B into the mixture A. In an embodiment, mixture A is slowly added to mixture B and then blended using a mixing machine of a rotor stator blender variety, which is operated at approximately 2,000 to 3,000 rotations per minute for approximately 3 minutes. The range of mixing time can extend from 1 minute to 20 minutes and any increment therein.

Hence, the present application discloses an ink formulation for marking live tissue comprising a dispersion of carbon black particles. The ink formulations are stable mixtures and do not precipitate out in normal working conditions. Further, the encapsulation of carbon black pigments by using emulsifiers not only aids in dispersing the carbon black in water without the use of additives, but also allows for easier insertion of the ink formulation into tissue cells. The dispersion ink formulation of the present application does not require any viscosity increasing agents, surfactant, ceteareth 20, or anti-foaming agents. It should be appreciated that, while glycerin does have a very small impact on viscosity, it does not generate such a viscosity increase to have a discernable impact on the viscosity of the overall formulation. Hence, the viscosity of the ink formulation may be adjusted based on an application of the ink. Further, since the ink formulation of the present application contains minimal additives, the ink is safe for use with human tissue and is less likely to produce any adverse reactions.

Although the present inventions have been described with particular focus on the use of the ink formulation for marking portions of the GI tract during endoscopic and surgical procedures, the ink may also be used for making body art, such as tattoos. The ink formulation of the present invention may also be used for a plurality of other purposes, such as marking livestock and wild animals for study. Because dispersions yield a deeper color with a given application, relative to a suspension, embodiments disclosed herein may also be used as permanent cosmetics such as permanent eye liner, permanent eyebrow, permanent lip liner, and permanent nipple areola pigmentation to cover scars, burns, or Vitiligo. The deeper colors of dispersions make them more preferable because it takes multiple applications of a suspension to yield the same color concentration that a dispersion yields in a single application. This arises from the relative constitutions of a suspension and dispersion. Suspensions are not uniform throughout. Particulate matter slowly moves to the bottom as it precipitates out. In the case of dispersions, the solid matter is uniformly dispersed throughout, allowing an equally dark application of color.

Example One

In the case of mixtures of insoluble particles inside a water vehicle, it is believed that the stability of a dispersion is superior to that of a suspension. In a comparison of two like dispersion and suspension formulations, stability is related to the rate of sedimentation of the insoluble particles compared to concentration. As the sedimentation process occurs, the insoluble particles separate from the mixture by density. The stability of a leading suspension was compared to that of a leading dispersion. Both formulations comprise water and glycerol delivery systems for similar insoluble carbon particle in regards to size and the percentage in the formulation. For each formulation the consistency of the density was compared over a three week time. The resulting differences in consistency were compared to the uniform density. By concentration, the density of the dispersion formulation remained closer to its uniform over time. Over a short three week term, a dispersion of insoluble particles in a water matrix showed more stability than a suspension of like constitution.

In one embodiment, a series of density tests were performed on like dispersion and suspension formulations of similar concentrations of carbon particles in a less dense liquid matrix. In each test, the top layer was removed and the density was measured. The top layer density was then compared to the density of the bottom layer. It was expected that, in dispersion formulations, the densities of the two layers would remain about the same. It was also expected that, in suspension formulations, there should be a significantly higher density in the bottom layer when compared to the density of the top layer, and, that density would increase with time. The density is a reflection of the concentration of insoluble particles and the precipitation rate of the particles. The uniformity of the density is dependent on the stability of the formulation.

Both formulations were mostly water-based formulations with between 0.9% and 1.1% carbon black. The suspension formulation was a suspension of high purity carbon particles in a medium of water, glycerol, polysorbate 80, benzyl alcohol, and simethicone. Glycerol acts as a thickener, simethicone acts as a dispersing aid, polysorbate 80 is an emulsifier and benzyl alcohol is a preservative. Samples were taken from individually sealed 5 ml syringes believed to be of the same lot number. The dispersion formulation was a mixture of encapsulated carbon particles in a medium of water, phenoxyethanol, and glycerol. The encapsulation consisted of glycerol, lecithin, and PVP. The phenoxyethanol acts as a preservative and glycerol acts to both aid encapsulation and cater the density of the formulation to the formulation's use. Samples were taken from a 200 ml bottle and were of the same lot number.

An analytical balance was used for all weights obtained. The scale was properly calibrated and its accuracy evaluated with a test weight prior to each measurement. The entire test took three weeks to perform. At the beginning of the first week, twenty sample vials were filled. Both formulations were shaken vigorously prior to filling the vials. Ten samples of each formulation were filled and stored in 5 ml graduated vials. The vials were equipped with an air lock top and stored in a cool, dry, level cabinet. The vials were not moved throughout their storage time to allow for sedimentation without agitation. At the end of each week, three 5 ml samples of each formulation were used for the density test and the results from each sample were averaged. During each density test, the top 2.900 to 3.100 ml were pipetted from the top layer and the weight recorded. The vial remained unmoved until the top layer was extracted. Then the volume and weight were taken from the remaining sample. The density of the top layer and bottom layer could then be compared.

The initial test at the beginning of week 1 showed no difference between the top and the bottom layers. The density of both layers of the suspension was 1.097 g/ml. The density of both layers of the dispersion was 1.029 g/ml. This initial calculation was not used in the calculation of the trend line. The average densities, difference in density (d), and difference in density (d) divided by the overall density multiplied by 100, measured after each of the three weeks of the study, are listed in Table 1 for the suspension formulation and Table 2 for the dispersion formulation.

TABLE 1

Suspension Formulation

|  | week 1 | week 2 | week 3 |
| --- | --- | --- | --- |
| Average Density | 1.082 g/ml | 1.106 g/ml | 1.088 g/ml |
| Average Density of Top Layer | 1.011 g/ml | 1.028 g/ml | 1.014 g/ml |
| Average Density of Bottom Layer | 1.105 g/ml | 1.155 g/ml | 1.189 g/ml |
| Difference in Density (d) | 0.094 g/ml | 0.127 g/ml | 0.175 g/ml |
| d/Overall Density * 100 | 8.686 | 11.448 | 16.130 |

After week 1, the average density of the suspension formulation was 1.082 g/ml. The average density of the top layer was 1.011 g/ml while the average density of the bottom layer was 1.105 g/ml, resulting in a difference in density (d) of 0.094 g/ml for the suspension formulation. The difference in density (d) divided by the overall density multiplied by 100 was 8.686 for the suspension formulation for week 1.

After week 2, the average density of the suspension formulation was 1.106 g/ml. The average density of the top layer was 1.028 g/ml while the average density of the bottom layer was 1.155 g/ml, resulting in a difference in density (d) of 0.127 g/ml for the suspension formulation. The difference in density (d) divided by the overall density multiplied by 100 was 11.448 for the suspension formulation for week 2.

After week 3, the average density of the suspension formulation was 1.088 g/ml. The average density of the top layer was 1.014 g/ml while the average density of the bottom layer was 1.189 g/ml, resulting in a difference in density (d) of 0.175 g/ml for the suspension formulation. The difference in density (d) divided by the overall density multiplied by 100 was 16.130 for the suspension formulation for week 3.

TABLE 2

Dispersion Formulation

|  | week 1 | week 2 | week 3 |
| --- | --- | --- | --- |
| Average Density | 1.020 g/ml | 1.024 g/ml | 1.029 g/ml |
| Average Density of Top Layer | 1.003 g/ml | 1.011 g/ml | 1.016 g/ml |
| Average Density of Bottom Layer | 1.047 g/ml | 1.045 g/ml | 1.048 g/ml |
| Difference in Density (d) | 0.044 g/ml | 0.035 g/ml | 0.032 g/ml |
| d/Overall Density * 100 | 4.351 | 3.369 | 3.110 |

After week 1, the average density of the dispersion formulation was 1.020 g/ml. The average density of the top layer was 1.003 g/ml while the average density of the bottom layer was 1.047 g/ml, resulting in a difference in density (d) of 0.044 g/ml for the dispersion formulation. The difference in density (d) divided by the overall density multiplied by 100 was 4.351 for the dispersion formulation for week 1.

After week 2, the average density of the dispersion formulation was 1.024 g/ml. The average density of the top layer was 1.011 g/ml while the average density of the bottom layer was 1.045 g/ml, resulting in a difference in density (d) of 0.035 g/ml for the dispersion formulation. The difference in density (d) divided by the overall density multiplied by 100 was 3.369 for the dispersion formulation for week 2.

After week 3, the average density of the dispersion formulation was 1.029 g/ml. The average density of the top layer was 1.016 g/ml while the average density of the bottom layer was 1.048 g/ml, resulting in a difference in density (d) of 0.032 g/ml for the dispersion formulation. The difference in density (d) divided by the overall density multiplied by 100 was 3.110 for the dispersion formulation for week 1.

The overall density of the formulations explains a great deal about the quantity of each ingredient in the formulation. Both formulations are known to be mostly water with approximately the same amount of carbon black in each. The density difference between the two formulations is due to the difference in the quantities and densities of the additives. From the slightly higher density of the suspension formula it can be speculated that it incorporated more additives or denser additives than the dispersion. This supports the theory that suspensions require more additives than do like dispersions.

The suspension showed a greater difference in densities than expected in a short term study, as seen in Table 1. It would seem that the glycerol, polysorbate 80, and all other denser ingredients migrated toward the bottom layer, along with a significant amount of the carbon black particles. This can be concluded because the density of the top layer approaches that of water while the density of the bottom layer approaches that of glycerol (1.261 g/ml). A significant amount of sedimentation occurred.

Figure 2:
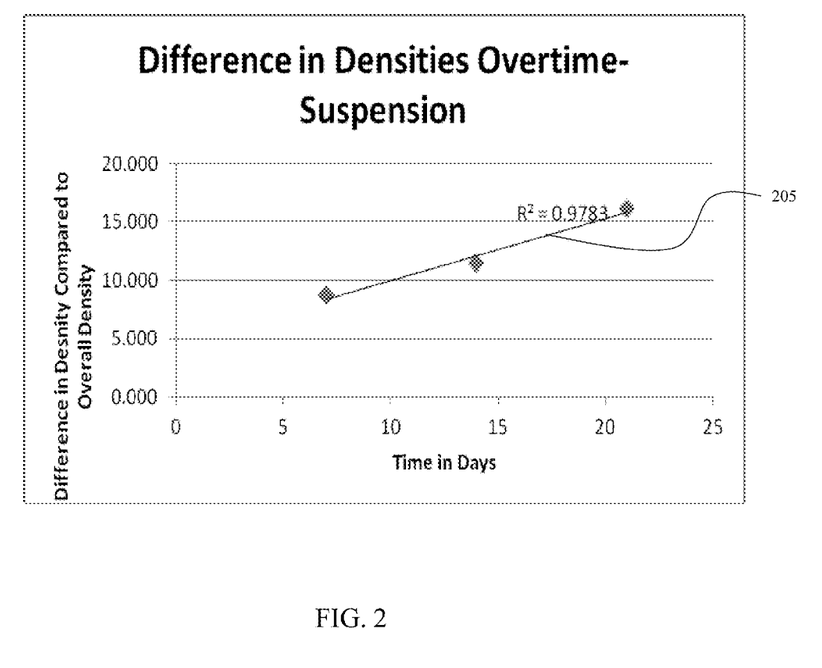
FIG. 2 is a line graph depicting the difference in densities over time versus the difference in density compared to the overall density for the suspension formulations of an exemplary ink formulation density study, in accordance with one embodiment of the present application; and, FIG. 3 is a line graph depicting the difference in densities over time versus the difference in density compared to the overall density for the dispersion formulations of an exemplary ink formulation density study, in accordance with one embodiment of the present application.

FIG. 2 is a line graph depicting the difference in densities over time versus the difference in density compared to the overall density for the suspension formulations of the study, in accordance with one embodiment of the present application. The $R^2$-value of the suspension trend line 205 suggests a correlation between the sedimentation and the time allowed to sediment in a short time-span study. The sedimentation process continued at a constant rate which suggests that this system follows Stoke's law. The overall densities differ but there is still a trend for the amount of sedimentation to increase over time. Insoluble particles are the main contributor to the sediment. It can be speculated that the differences in densities is due to differing amounts of soluble particles because this would have the least affect on the trend.

Figure 3:
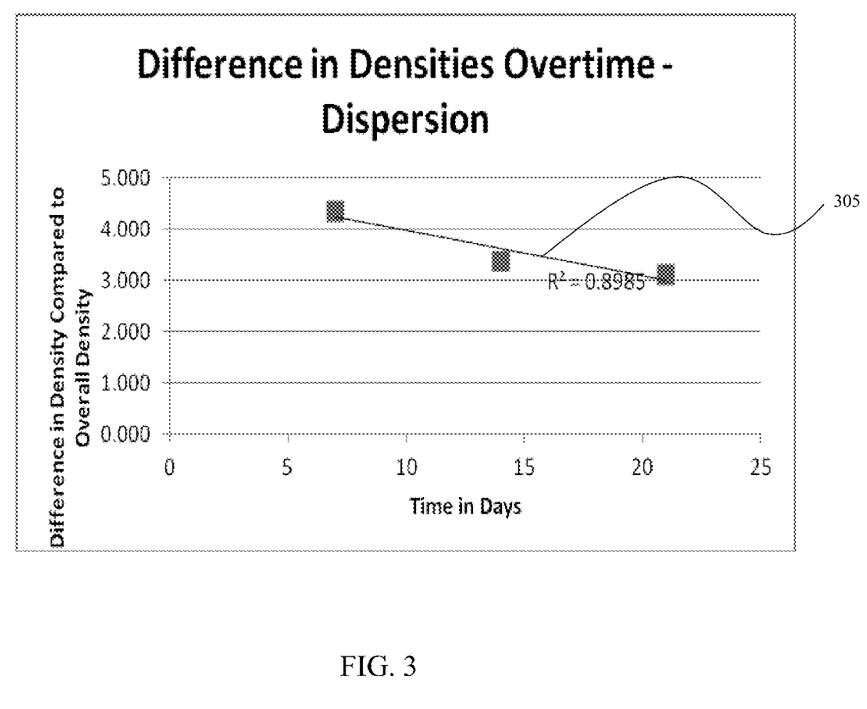

FIG. 3 is a line graph depicting the difference in densities over time versus the difference in density compared to the overall density for the dispersion formulations of the study, in accordance with one embodiment of the present application. The dispersion showed sedimentation but the amount of sediment remained fairly constant regardless of time. The $R^2$ value of the dispersion trend line 305 was not as close to that of the suspension. It can be speculated that all of the short term sedimentation process takes place within seven days. The lack of change supports the theory that dispersions do not follow normal laws of suspensions such as Stoke's law.

Sedimentation was seen in both the dispersion and the suspension. When the amount of sedimentation in each formulation was compared with that formulation's original density, the amount of sedimentation in each formulation could then be compared. The suspension showed a great deal of sedimentation in total, compared to the total formulation density. This rate of sedimentation was constant over the three weeks showing that the process of sedimentation continued throughout the study. The dispersion showed much less sediment compared to the overall formulation density. The amount of sediment did not increase with time. Over a short time period the density of the dispersion formulation remained more uniform than the like suspension formulation. The dispersion formulation is more stable over a short time frame.

The above examples are merely illustrative of the many applications of the compositions and manufacturing methods of the present application. Although only a few embodiments have been described herein, it should be understood that the disclosed inventions might be embodied in many other specific forms without departing from the spirit or scope of the invention. Therefore, the present examples and embodiments are to be considered as illustrative and not restrictive.

We claim:

1. An ink formulation for marking living tissue, wherein said ink formulation is made by the following process:
   a. mixing a pharmaceutically accepted carrier with a preservative to form a carrier-preservative compound;
   b. pre-wetting a carbon pigment with a first emulsifying agent;
   c. mixing a second emulsifying agent with glycerin to form an emulsifier-glycerin compound;
   d. adding said emulsifier-glycerin compound to the pre-wet carbon and mixing until encapsulated carbon particles are formed; and,
   e. mixing said carrier-preservative compound with said encapsulated carbon particles to form said ink formulation.

2. The ink formulation for marking living tissue of claim 1, wherein said pharmaceutically accepted carrier is water.

3. The ink formulation for marking living tissue of claim 2, wherein said water comprises between 85.00 and 92.00% of the total formulation by weight.

4. The ink formulation for marking living tissue of claim 2, wherein said water comprises 91.73% of the total formulation by weight.

5. The ink formulation for marking living tissue of claim 1, wherein said preservative is selected from the group comprising of 2-phenoxyethanol, benzyl alcohol, methyl/propyl paraben blend, and polyaminopropyl biguanide.

6. The ink formulation for marking living tissue of claim 5, wherein said preservative comprises between 1.00 and 1.50% of the total formulation by weight.

7. The ink formulation for marking living tissue of claim 5, wherein said preservative comprises 1.24% of the total formulation by weight.

8. The ink formulation for marking living tissue of claim 1, wherein said carbon pigment is carbon black and the carbon black contains PAH in a range of 0.5 ppm or more.

9. The ink formulation for marking living tissue of claim 8, wherein said carbon black comprises between 1.09 and 1.10% of the total formulation by weight.

10. The ink formulation for marking living tissue of claim 8, wherein said carbon black comprises 1.09% of the total formulation by weight.

11. The ink formulation for marking living tissue of claim 1, wherein said first and second emulsifying agents are selected from the group comprising of lecithin, soy lecithin, PVP, emulsifying wax, and polysorbate 20.

12. The ink formulation for marking living tissue of claim 11, wherein said first and second emulsifying agents comprise between 0.20 and 0.30% and between 1.00 and 2.50% respectively, of the total formulation by weight.

13. The ink formulation for marking living tissue of claim 11, wherein said first and second emulsifying agents comprise 0.24% and 2.50% respectively, of the total formulation by weight.

14. The ink formulation for marking living tissue of claim 1, wherein said glycerin comprises between 2.50 and 4.50% of the total formulation by weight.

15. The ink formulation for marking living tissue of claim 1, wherein said glycerin comprises between 3.15% of the total formulation by weight.

16. A method of preparing an ink formulation for marking living tissue, comprising the steps of:
   a. mixing a pharmaceutically accepted carrier with a preservative to form a carrier-preservative compound;
   b. pre-wetting a carbon pigment with a first emulsifying agent;
   c. mixing a second emulsifying agent with glycerin to form an emulsifier-glycerin compound;
   d. adding said emulsifier-glycerin compound into the pre-wet carbon and mixing until said carbon is dispersed; and,
   e. mixing said carrier-preservative compound to said dispersed carbon.

17. The method of preparing an ink formulation for marking living tissue of claim 16, wherein the mixing of said pharmaceutically accepted carrier with said preservative is performed at a high speed for approximately 2 minutes.

18. The method of preparing an ink formulation for marking living tissue of claim 16, wherein the pre-wetting of said carbon pigment with said first emulsifying agent and the mixing of said second emulsifying agent with glycerin are performed separately and wherein both the pre-wetting of said carbon pigment with said first emulsifying agent and the mixing of said second emulsifying agent with glycerin are performed utilizing a homogenizer.

19. An ink formulation for use on living tissue, having a total weight, comprising
   a. a pharmaceutically acceptable carrier, wherein said pharmaceutically acceptable carrier is in a range of 85% to 92% of the total weight;
   b. a preservative, wherein said preservative is in a range of 1.0% to 1.5% of the total weight; and
   c. carbon black, wherein said carbon black is in a range of 1.09% to 1.10% of the total weight, wherein particles of said carbon black are encapsulated by at least one of lecithin, soy lecithin, polyvinylpyrrolidone (PVP), emulsifying wax, polysorbate 20, or glycerin, wherein said ink formulation is a dispersion of said preservative and carbon black in the carrier, and wherein the formulation does not include suspending agents, viscosity agents, surfactants, ceteareth 20, or antifoaming agents.

20. The ink formulation of claim 19 wherein the carrier is water and the preservative is one of 2-phenoxyethanol, benzyl alcohol, methyl/propyl paraben blend, or polyaminopropyl biguanide.

* * * * *